United States Patent
Tanaka et al.

(10) Patent No.: US 10,525,014 B2
(45) Date of Patent: Jan. 7, 2020

(54) PATCH

(71) Applicant: KANEKA CORPORATION, Osaka-shi (JP)

(72) Inventors: Tatsuyoshi Tanaka, Takasago (JP); Masaya Mizutani, Takasago (JP); Hiroyuki Ogino, Takasago (JP); Mitsuji Akazawa, Takasago (JP); Akio Fujii, Takasago (JP); Naohiro Imai, Takasago (JP)

(73) Assignee: KANEKA CORPORATION, Osaka-shi (JP)

( * ) Notice: Subject to any disclaimer, the term of this patent is extended or adjusted under 35 U.S.C. 154(b) by 0 days.

(21) Appl. No.: 15/750,669

(22) PCT Filed: Aug. 5, 2016

(86) PCT No.: PCT/JP2016/073068
§ 371 (c)(1),
(2) Date: Feb. 6, 2018

(87) PCT Pub. No.: WO2017/026386
PCT Pub. Date: Feb. 16, 2017

(65) Prior Publication Data
US 2018/0235902 A1    Aug. 23, 2018

(30) Foreign Application Priority Data

Aug. 7, 2015 (JP) .................................. 2015-157482

(51) Int. Cl.
| | | |
|---|---|---|
| *A61K 9/70* | (2006.01) | |
| *A61K 31/167* | (2006.01) | |
| *A61P 23/02* | (2006.01) | |
| *A61K 9/00* | (2006.01) | |

(52) U.S. Cl.
CPC .......... *A61K 9/7053* (2013.01); *A61K 9/0014* (2013.01); *A61K 9/7076* (2013.01); *A61K 31/167* (2013.01); *A61P 23/02* (2018.01)

(58) Field of Classification Search
CPC .. A61K 31/167; A61K 9/7076; A61K 9/7053; A61K 9/0014; A61P 23/02
See application file for complete search history.

(56) References Cited

U.S. PATENT DOCUMENTS

| | | | | |
|---|---|---|---|---|
| 5,446,070 A | * | 8/1995 | Mantelle | A61K 9/006 424/485 |
| 5,741,510 A | * | 4/1998 | Rolf | A61K 9/7061 424/448 |
| 6,953,590 B1 | * | 10/2005 | Owaki | A61K 9/7053 424/449 |
| 2011/0319975 A1 | * | 12/2011 | Ho | A61N 1/0408 607/139 |
| 2013/0184351 A1 | * | 7/2013 | Ciullo | A61K 31/167 514/626 |
| 2013/0224262 A1 | * | 8/2013 | Akazawa | A61K 9/7053 424/400 |
| 2016/0101166 A1 | * | 4/2016 | Salamone | A61K 38/47 424/94.2 |

FOREIGN PATENT DOCUMENTS

| | | |
|---|---|---|
| JP | 54-101414 A | 8/1979 |
| JP | 60-204714 A | 10/1985 |
| JP | 8-319234 A | 12/1996 |
| JP | 2000-178186 A | 6/2000 |
| JP | 2010-222312 A | 10/2010 |
| JP | 2013-116861 A | 6/2013 |
| JP | 2016-3196 A | 1/2016 |
| WO | WO 2012/029097 A1 | 3/2012 |

OTHER PUBLICATIONS

Cherukuvada et al. ("Eutectics as improved pharmaceutical materials: design, properties and characterization" in ChemComm, Royal Society of Chemistry, 2014, vol. 50, pp. 906-923).*
Hideo et al. (JPS60204714 (A), translation provided by applicant on IDS), 1985.*
Hiroyuki et al. (JPH08319234(A), translation provided by applicant on IDS) , 1996.*
International Search Report dated Sep. 27, 2016 in PCT/JP2016/073068 (with English translation), citing documents AA, AB, AK—AO and AU therein, 7 pages.
International Preliminary Report on Patentability and Written Opinion of the International Searching Authority dated Feb. 22, 2018 in PCT/JP2016/073068 filed Aug. 5, 2016 (with English translation), citing documents AA, AB, AK—AN and AU therein, 14 pages.
Suryanarayan Cherukuvada, et al., "Eutectics as Improved Pharmaceutical Materials: Design, Properties and Characterization" Chemical Communications, vol. 50, 2014, pp. 906-923 and Cover pages.
Kazuya Ooi, "Differences of Pain Anesthetic Effect Expression on Using Lidocaine Tape in Hemodialysis Patients" The Pharmaceutical Society of Japan, vol. 127, No. 11, 2007, pp. 1797-1799.
Nanna Brix Finnerup, et al., "The Evidence for Pharmacological Treatment of Neuropathic Pain" Pain, vol. 150, No. 3, 2010, pp. 573-581.

(Continued)

*Primary Examiner* — Blessing M Fubara
(74) *Attorney, Agent, or Firm* — Oblon, McClelland, Maier & Neustadt, L.L.P.

(57) ABSTRACT

It is an object of the present invention to provide a patch having practical adhesive force and cohesive force as a pharmaceutical product, and also exhibiting a fast-acting anesthetic action. The present invention provides a patch formed from an adhesive layer comprising 5% by weight or more and less than 20% by weight of a mixture of lidocaine and another local anesthetic, wherein the adhesive layer comprises at least a rubber-based pressure-sensitive adhesive and liquid paraffin and a content of a tackifier in the adhesive layer is 10% by weight or less.

13 Claims, 1 Drawing Sheet

(56) References Cited

OTHER PUBLICATIONS

Sun Ho Kim, et al., "An Experimental Model for Peripheral Neuropathy Produced by Segmental Spinal Nerve Ligation in the Rat" PAIN, vol. 50, No. 3, 1992, pp. 355-363.

Extended European Search Report dated Feb. 19, 2019 in corresponding European Patent Application No. 16835083.3 citing document AA therein, 9 pages.

* cited by examiner

[Figure 1]
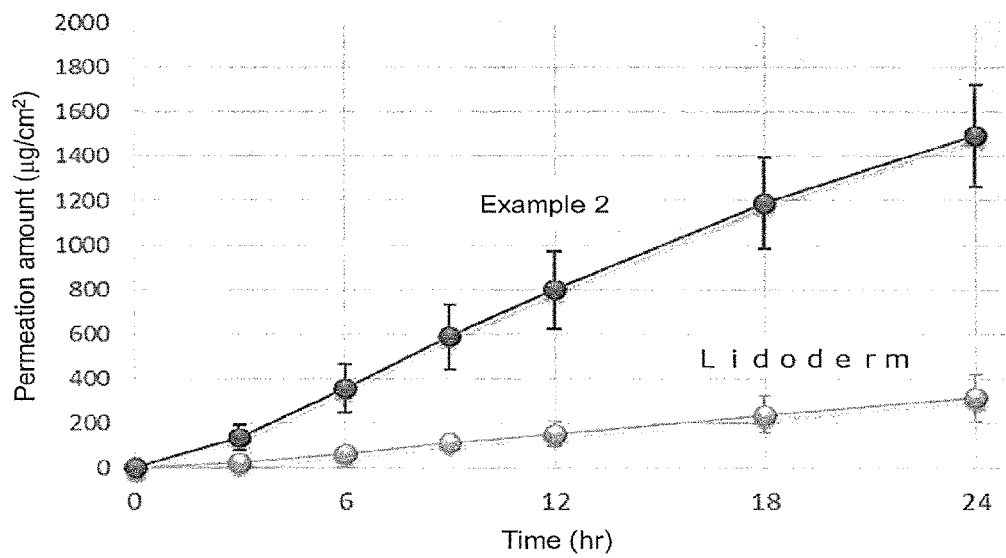
[Figure 2]
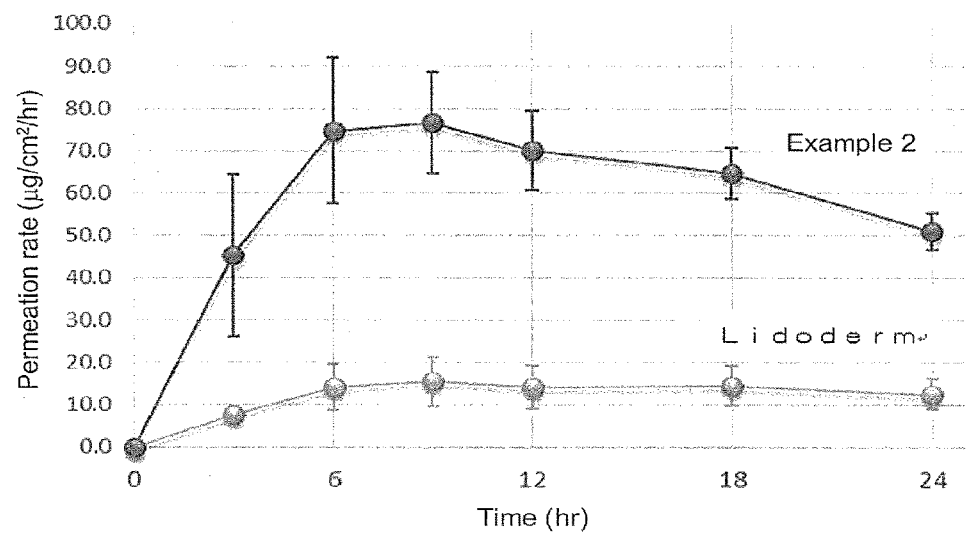

PATCH

TECHNICAL FIELD

The present invention relates to a patch that can be used for local anesthesia.

BACKGROUND ART

Local anesthetic formulation, which is one type of transdermal absorption formulation, has been widely used for the purpose of relieving pain generated during a medical treatment such as intravenous indwelling needle puncture or skin minor surgery. In Japan, as such a local anesthetic formulation, a tape agent of lidocaine (Penles (registered trademark)) has been commercially available. This tape agent is a formulation prepared by allowing an acrylic pressure-sensitive adhesive to comprise lidocaine crystals (concentration: 60%), and according to the Package insert of this tape agent, it is described that when the agent is used for pain relief during intravenous indwelling needle puncture, it is attached to the puncture target site for approximately 30 minutes. However, it has also been reported that, in order to obtain sufficient effects of pain relieving, it is necessary to attach the agent for 100 minutes on average (Non Patent Literature 1). Hence, from the viewpoint of medication management or a problem regarding an increase in burden on patients, it has been desired to reduce the time, at which anesthetic effects are expressed, in actual medical sites.

On the other hand, as transdermal absorption preparations for local anesthesia, combination drugs each comprising two types of local anesthetics, such as a mixture of lidocaine and prilocaine or a mixture of lidocaine and tetracaine, have been proposed. It has been known that such a combination drug exhibits an excellent local anesthetic action, when compared with administration of a single local anesthetic agent. In fact, a cream formulation (Emla Cream), oil in water emulsion of a mixture of lidocaine and prilocaine, has been commercially available, and this cream formulation has been confirmed to have a higher anesthetic action than a cream formulation comprising lidocaine alone and prilocaine alone (Patent Literature 1). However, in order to achieve sufficient pain relieving effects from this cream agent, it has been necessary to spread the present cream agent to the skin such that the cream is thickly heaped up thereon, and further, to apply an occlusive dressing technique (ODT) using a film or the like. Thus, this cream agent has been problematic in terms of complicated procedures.

In view of the foregoing, a simple tape agent comprising a mixture of lidocaine and prilocaine as a drug has also been proposed (Patent Literature 2). Patent Literature 2 discloses a prescription of using a crosslinked acrylic pressure-sensitive adhesive, and when compared with the previous lidocaine tape agent (Penles (registered trademark)), this formulation has been confirmed to have the fast-acting property of anesthesia. Nevertheless, as a result of the studies conducted by the present inventors, it has been revealed that the skin permeability of the drug (in vitro test) used as an indicator of the expression of medicinal effects is inferior to the previous cream agent, and that the skin permeability is approximately 2 times higher than that of Penles (registered trademark).

Moreover, as a local anesthetic, a water-soluble patch comprising a mixture of lidocaine and prilocaine or a mixture of lidocaine and tetracaine has also been proposed (Patent Literature 3). But in general, such a water-soluble patch has been problematic in that its adhesiveness is lower than that of a water-insoluble tape agent, and thus, it is easily dropped out from the skin.

Shingles is a disease, which is caused by infection with varicella or shingles virus, and skin rash is generated along the dermatome of an area supplied by a nerve, and pain also appears due to such skin rash. In a majority of shingles patients, such pain disappears with the recovery of skin rash. In some patients, however, shingles is shifted to postherpetic neuralgia, in which pain remains even after the recovery of skin rash. Postherpetic neuralgia is caused by the damage or degeneration of the peripheral nervous fibers of a patient infected with varicella or shingles virus, and this disease is classified into neuropathic pain. Since intolerable pain symptoms such as shooting pain or allodynia, which are hardly experienced in daily life, continuously occur, the QOL of patients with postherpetic neuralgia is significantly reduced. With regard to the aforementioned water-soluble patch, Lidoderm (a 5% lidocaine poultice preparation, Endo Pharmaceuticals Inc.) has been placed on the market as a therapeutic agent for postherpetic neuralgia in the United States of America, and according to the guidelines of International Association for the Study of Pain, Lidoderm is determined to be a first-line drug for superficially localized neuropathic pain. However, taking into consideration its long application time such as attachment for 12 hours, this patch agent always has the risk of being dropped out from the skin because of its weak adhesive force, and thus, it is highly likely that the original therapeutic effects cannot be obtained due to such dropping out. In addition, since the therapeutic effects of Lidoderm are not necessarily high (Non Patent Literature 2), it has been desired to develop a patch having higher therapeutic effects for postherpetic neuralgia.

PRIOR ART LITERATURES

Patent Literatures

Patent Literature 1: JP Patent Publication (Kokai) No. 54-101414 A (1979)
Patent Literature 2: JP Patent Publication (Kokai) No. 2010-222312 A
Patent Literature 3: JP Patent Publication (Kokai) No. 2013-116861 A

Non Patent Literatures

Non Patent literature 1: YAKUGAKU ZASSIII 127(11) 1797-1799 (2007)
Non Patent Literature 2: PAIN 150(3), 573-581 (2010)

SUMMARY OF INVENTION

Object to be Solved by the Invention

It is an object of the present invention to provide a patch having practical adhesive force and cohesive force as a pharmaceutical product, and also exhibiting a fast-acting anesthetic action.

Means for Solving the Object

As a result of intensive studies directed towards achieving the aforementioned object, the present inventors have elucidated that a rubber-based adhesive layer containing 10% by weight or less of a tackifier is allowed to comprise "lidocaine and another local anesthetic" as drugs, so as to realize a patch having extremely high skin permeability of drugs. In general, when a rubber-based pressure-sensitive adhesive is used, if a content of a tackifier is small, it is difficult to realize a formulation having adhesive force that is sufficient as a pharmaceutical product. However, the present inventors surprisingly have found that a "mixture of lidocaine and another local anesthetic" contributes to the maintenance and improvement of such adhesive force, thereby completing a fast-acting local anesthetic formulation having sufficiently high adhesive force and cohesive force. Specifically, the summary of the present invention is as follows.

(1) A patch formed from an adhesive layer comprising 5% by weight or more and less than 20% by weight of a mixture of lidocaine and another local anesthetic, wherein the adhesive layer comprises at least a rubber-based pressure-sensitive adhesive and liquid paraffin and a content of a tackifier in the adhesive layer is 10% by weight or less.

(2) The patch according to the above (1), wherein the liquid paraffin is comprised in an amount of 0.5 times by weight or more and 2.6 times by weight or less based on an amount of the rubber-based pressure-sensitive adhesive.

(3) The patch according to the above (1), wherein the liquid paraffin is comprised in an amount of 0.6 times by weight or more and 2.0 times by weight or less based on an amount of the rubber-based pressure-sensitive adhesive.

(4) The patch according to the above (1), wherein the liquid paraffin is comprised in an amount of 0.7 times by weight or more and 1.5 times by weight or less based on an amount of the rubber-based pressure-sensitive adhesive.

(5) The patch according to any one of the above (1) to (4), wherein the rubber-based pressure-sensitive adhesive is a styrene-based block copolymer.

(6) The patch according to the above (5), wherein the rubber-based pressure-sensitive adhesive is a mixture of a styrene-isoprene-styrene block copolymer and a styrene-isoprene block copolymer.

(7) The patch according to the above (6), wherein a content of the styrene-isoprene-styrene copolymer in the mixture of a styrene-isoprene-styrene block copolymer and a styrene-isoprene block copolymer is 15% by weight or more and 60% by weight or less.

(8) The patch according to the above (6), wherein a content of the styrene-isoprene-styrene copolymer in the mixture of a styrene-isoprene-styrene block copolymer and a styrene-isoprene block copolymer is 20% by weight or more and 50% by weight or less.

(9) The patch according to the above (1), wherein the liquid paraffin is comprised in an amount of 2.0 times by weight or more and 6.0 times by weight or less based on an amount of the rubber-based pressure-sensitive adhesive.

(10) The patch according to the above (1), wherein the liquid paraffin is comprised in an amount of 2.3 times by weight or more and 5.5 times by weight or less based on an amount of the rubber-based pressure-sensitive adhesive.

(11) The patch according to the above (1), wherein the liquid paraffin is comprised in an amount of 2.6 times by weight or more and 5.0 times by weight or less based on an amount of the rubber-based pressure-sensitive adhesive.

(12) The patch according to any one of the above (9) to (11), wherein the rubber-based pressure-sensitive adhesive is a styrene-based block copolymer.

(13) The patch according to the above (12), wherein the rubber-based pressure-sensitive adhesive is a mixture of a styrene-isoprene-styrene block copolymer and a styrene-isoprene block copolymer.

(14) The patch according to the above (13), wherein a content of the styrene-isoprene-styrene copolymer in the mixture of a styrene-isoprene-styrene block copolymer and a styrene-isoprene block copolymer is 60% by weight or more and 95% by weight or less.

(15) The patch according to the above (13), wherein a content of the styrene-isoprene-styrene copolymer in the mixture of a styrene-isoprene-styrene block copolymer and a styrene-isoprene block copolymer is 70% by weight or more and 90% by weight or less.

(16) The patch according to the above (1), wherein the rubber-based pressure-sensitive adhesive is a mixture of a styrene-isoprene-styrene block copolymer and a styrene-isoprene block copolymer, and when a weight of the liquid paraffin to a weight of the rubber-based pressure-sensitive adhesive is defined as y, a weight percent of the styrene-isoprene-styrene copolymer in the mixture of a styrene-isoprene-styrene block copolymer and a styrene-isoprene block copolymer is defined as x, and the base of natural logarithm is defined as e, the patch satisfies the following exponential: $0.48e^{0.022x} - 0.4 \leq y \leq e^{0.021x} + 0.4$.

(17) The patch according to the above (1), wherein the rubber-based pressure-sensitive adhesive is a mixture of a styrene-isoprene-styrene block copolymer and a styrene-isoprene block copolymer, and when a weight of the liquid paraffin to a weight of the rubber-based pressure-sensitive adhesive is defined as y, a weight percent of the styrene-isoprene-styrene copolymer in the mixture of a styrene-isoprene-styrene block copolymer and a styrene-isoprene block copolymer is defined as x, and the base of natural logarithm is defined as e, the patch satisfies the following exponential: $0.48e^{0.022x} - 0.2 \leq y \leq e^{0.021x} + 0.2$.

(18) The patch according to the above (1), wherein the rubber-based pressure-sensitive adhesive is a mixture of a styrene-isoprene-styrene block copolymer and a styrene-isoprene block copolymer, and when a weight of the liquid paraffin to a weight of the rubber-based pressure-sensitive adhesive is defined as y, a weight percent of the styrene-isoprene-styrene copolymer in the mixture of a styrene-isoprene-styrene block copolymer and a styrene-isoprene block copolymer is defined as x, and the base of natural logarithm is defined as e, the patch satisfies the following exponential: $0.48e^{0.022x} \leq y \leq e^{0.021x}$.

(19) The patch according to any one of the above (1) to (18), wherein said another local anesthetic is prilocaine, tetracaine or benzocaine.

(20) The patch according to the above (19), wherein a content of the lidocaine in the mixture of lidocaine and another local anesthetic is 30% by weight or more and 70% by weight or less.

(21) The patch according to the above (19), wherein a content of the lidocaine in the mixture of lidocaine and another local anesthetic is 40% by weight or more and 60% by weight or less.

(22) The patch according to the above (19), wherein a content of the lidocaine in the mixture of lidocaine and another local anesthetic is 45% by weight or more and 55% by weight or less.

(23) The patch according to the above (19), wherein a weight ratio of the lidocaine and the another local anesthetic in the mixture is 50/50.

(24) The patch according to any one of the above (19) to (23), wherein a content of the mixture of lidocaine and another local anesthetic is 5% by weight or more and less than 15% by weight, based on the total amount of pressure-sensitive adhesive components.

(25) The patch according to any one of the above (1) to (24), wherein the adhesive layer does not comprise a tackifier.
(26) The patch according to any one of the above (1) to (25), which is used as a local anesthetic agent.
(27) The patch according to any one of the above (1) to (26), which is used as an analgesic or a pain therapeutic agent.
(28) The patch according to the above (27), which is used as a therapeutic agent for neuropathic pain.
(29) The patch according to the above (27), which is used as a therapeutic agent for postherpetic neuralgia.
(30) A local anesthetic method comprising a step of attaching the patch according to any one of the above (1) to (29) to the affected area of a patient in need of local anesthesia.
(31) A method for pain relief or pain treatment, comprising a step of attaching the patch according to any one of the above (1) to (29) to the affected area of a patient in need of pain relief or pain treatment.
(32) The method according to the above (31), wherein the pain is neuropathic pain.
(33) The method according to the above (31), wherein the pain is postherpetic neuralgia.
(34) Use of the patch according to any one of the above (1) to (29) for the production of a local anesthetic agent.
(35) Use of the patch according to any one of the above (1) to (29) for the production of an analgesic or a pain therapeutic agent.
(36) The use according to the above (35), wherein the pain therapeutic agent is a therapeutic agent for neuropathic pain.
(37) The use according to the above (35), wherein the pain therapeutic agent is a therapeutic agent for postherpetic neuralgia.

Advantageous Effects of Invention

According to the present invention, a patch for local anesthesia, which can realize fast-acting anesthetic effects, can be provided.

BRIEF DESCRIPTION OF DRAWINGS

FIG. 1 shows the results obtained by measuring a cumulative drug skin permeation amount in the evaluation of in vitro rat skin permeability.
FIG. 2 shows the results obtained by measuring a drug skin permeation rate in the evaluation of in vitro rat skin permeability.

EMBODIMENTS FOR CARRYING OUT THE INVENTION

Hereinafter, the present invention will be described in detail. The patch of the present invention preferably has a backing and at least one pressure-sensitive adhesive layer established on the backing.

The pressure-sensitive adhesive layer used in the present invention comprises (a) a mixture of lidocaine and another local anesthetic as a drug, and further comprises, at least, (b) a rubber-based pressure-sensitive adhesive, and (c) liquid paraffin.

(a) Mixture of Lidocaine and Another Local Anesthetic

Lidocaine that can be used in the present invention may be either lidocaine as a free base, or a pharmaceutically acceptable salt of lidocaine. The pharmaceutically acceptable salt is not particularly limited, and it may be either an inorganic salt or an organic salt. Examples of the inorganic salt of lidocaine include hydrochloride, hydrobromide, nitrate, sulfate, and phosphate. Examples of the organic salt of lidocaine include formate, acetate, trifluoroacetate, propionate, lactate, tartrate, oxalate, fumarate, maleate, citrate, malonate, and methanesulfonate. From the viewpoint of easy availability, lidocaine as a free base or lidocaine hydrochloride is preferably used. From the viewpoint of dispersibility in the pressure-sensitive adhesive, lidocaine as a free base is particularly preferably used.

Another local anesthetic that can be used in the present invention is not particularly limited, as long as it has a basic skeleton consisting of an aromatic ring, an alkyl chain and an amino group, and also has a structure in which the aromatic ring binds to the alkyl chain via an ester bond or an amide bond. Examples of such another local anesthetic include prilocaine, tetracaine, benzocaine, bupivacaine, and mepivacaine. The above-described another local anesthetic can preferably be a local anesthetic, which is present in the form of a solid at room temperature, but when it is mixed with another solid lidocaine, the melting point thereof has decreased and it is liquefied at ambient temperature.

The mixture of lidocaine and another local anesthetic is preferably a mixture of lidocaine and prilocaine, a mixture of lidocaine and tetracaine, or a mixture of lidocaine and benzocaine, and is more preferably a mixture of lidocaine and prilocaine or a mixture of lidocaine and tetracaine.

A content of the lidocaine in the mixture of lidocaine and another local anesthetic is preferably 30% by weight or more and 70% by weight or less, more preferably 40% by weight or more and 60% by weight or less, further preferably 45% by weight or more and 55% by weight or less, and most preferably, the weight ratio between lidocaine and another local anesthetic in the mixture is 50/50.

A content of the lidocaine in the mixture of lidocaine and prilocaine is preferably 30% by weight or more and 70% by weight or less, more preferably 40% by weight or more and 60% by weight or less, and further preferably 45% by weight or more and 55% by weight or less. In particular, a reduction in the melting point becomes maximum, when lidocaine and prilocaine are mixed with each other at an equal weight ratio. Accordingly, a mixture of lidocaine and prilocaine, which has the weight ratio of 50/50, is most preferable.

A content of the lidocaine in the mixture of lidocaine and tetracaine is preferably 30% by weight or more and 70% by weight or less, more preferably 40% by weight or more and 60% by weight or less, and further preferably 45% by weight or more and 55% by weight or less. A mixture of lidocaine and tetracaine, which has the weight ratio of 50/50, is most preferable.

A content of the lidocaine in the mixture of lidocaine and benzocaine is preferably 20% by weight or more and 70% by weight or less, and more preferably 30% by weight or more and 70% by weight or less. Further, a content of the lidocaine in the mixture may be 40% by weight or more and 60% by weight or less, or may also be 45% by weight or more and 55% by weight or less. A mixture of lidocaine and benzocaine, which has the weight ratio of 30/70, is most preferable.

Prilocaine that can be used in the present invention may be either prilocaine as a free base, or a pharmaceutically acceptable salt of prilocaine. The pharmaceutically acceptable salt is not particularly limited, and examples of the pharmaceutically acceptable salt include those described in the above-described lidocaine. From the viewpoint of easy availability, prilocaine as a free base or prilocaine hydrochloride is preferably used. From the viewpoint of dispersibility in the pressure-sensitive adhesive, prilocaine as a free base is particularly preferably used.

Tetracaine that can be used in the present invention may be either tetracaine as a free base, or a pharmaceutically acceptable salt of tetracaine. The pharmaceutically acceptable salt is not particularly limited, and examples of the pharmaceutically acceptable salt include those described in the above-described lidocaine. From the viewpoint of easy availability, tetracaine as a free base or tetracaine hydrochloride is preferably used. From the viewpoint of dispersibility in the pressure-sensitive adhesive, tetracaine as a free base is particularly preferably used.

Benzocaine that can be used in the present invention may be either benzocaine as a free base, or a pharmaceutically acceptable salt of benzocaine. The pharmaceutically acceptable salt is not particularly limited, and examples of the pharmaceutically acceptable salt include those described in the above-described lidocaine. From the viewpoint of easy availability, benzocaine as a free base or benzocaine hydrochloride is preferably used. From the viewpoint of dispersibility in the pressure-sensitive adhesive, benzocaine as a free base is particularly preferably used.

By mixing the mixture of lidocaine and another local anesthetic with a rubber-based pressure-sensitive adhesive, adhesiveness sufficient as a pharmaceutical product can be obtained, even if a content of a tackifier is small.

In order to achieve sufficient medicinal effects, the mixed amount of the mixture of lidocaine and another local anesthetic is preferably 5% by weight or more, based on the total amount of pressure-sensitive adhesive components. The mixed amount of the mixture of lidocaine and another local anesthetic is more preferably 7% by weight or more. On the other hand, from the viewpoint of ensuring cohesive force, the upper limit of the mixed amount is preferably less than 20% by weight. It is more preferably less than 15% by weight, further preferably less than 12% by weight, and most preferably 10% by weight or less. It is to be noted that the term "pressure-sensitive adhesive components" is used in the present description to mean components that constitute the pressure-sensitive adhesive layer. The total amount of pressure-sensitive adhesive components indicates the amount of the entire formulation, from which a backing and a liner are excluded.

In the above-described ranges, the mixed amount of the mixture of lidocaine and another local anesthetic is preferably 5% by weight or more and less than 20% by weight, more preferably 5% by weight or more and less than 15% by weight, particularly preferably 5% by weight or more and less than 12% by weight, and most preferably 7% by weight or more and less than 12% by weight.

(b) Rubber-Based Pressure-Sensitive Adhesive

The rubber-based pressure-sensitive adhesive that can be used in the patch of the present invention is not particularly limited. Examples of such a rubber-based pressure-sensitive adhesive include a styrene-based block copolymer, polyisobutylene, natural rubber, butyl rubber, polyisoprene, and polybutene.

In particular, from the viewpoint of the achievement of sufficient drug release properties, cohesiveness and adhesiveness, which is the object of the present invention, a styrene-based block copolymer is particularly preferable. Specific examples of the styrene-based block copolymer include a styrene-butadiene block copolymer, a styrene-butadiene-styrene block copolymer, a styrene-isoprene block copolymer, a styrene-isoprene-styrene block copolymer, a styrene-ethylene/butylene block copolymer, a styrene-ethylene/butylene-styrene block copolymer, a styrene-ethylene/propylene block copolymer, a styrene-ethylene/propylene-styrene block copolymer, a styrene-isobutylene block copolymer, and a styrene-isobutylene-styrene block copolymer. It is to be noted that, in the above description, "ethylene/butylene" indicates a copolymer block of ethylene and butylene, and "ethylene/propylene" indicates a copolymer block of ethylene and propylene. These styrene-based block copolymers may be used alone, or in combination of two or more types.

Among the above-described styrene-based block copolymers, from the viewpoint of availability, one or two selected from the group consisting of a styrene-isoprene-styrene block copolymer and a styrene-isoprene block copolymer are preferably used. A mixture of a styrene-isoprene-styrene block copolymer and a styrene-isoprene block copolymer is particularly preferable.

In one example of the present invention, there may be a case where inconvenience is generated, such that skin adhesiveness tends to be decreased if the mixing ratio of the styrene-isoprene block copolymer to the styrene-isoprene-styrene copolymer is too low, or the shape-maintaining property of the pressure-sensitive adhesive layer tends to be decreased if the mixing ratio of the styrene-isoprene block copolymer to the styrene-isoprene-styrene copolymer is too high.

In one example of the present invention, the upper limit of the content of the styrene-isoprene-styrene block copolymer in the mixture of a styrene-isoprene-styrene block copolymer and a styrene-isoprene block copolymer is preferably 95% by weight or less. It may be 90% by weight or less, or 80% by weight or less, or 60% by weight or less, or 50% by weight or less. The lower limit thereof is preferably 10% by weight or more. It may be 15% by weight or more, or 20% by weight or more, or 50% by weight or more, or 60% by weight or more, or 70% by weight or more.

In one example of the present invention, a content of the styrene-isoprene-styrene block copolymer in the mixture of a styrene-isoprene-styrene block copolymer and a styrene-isoprene copolymer is preferably 10% by weight or more and 90% by weight or less, more preferably 15% by weight or more and 60% by weight or less, and most preferably 20% by weight or more and 50% by weight or less.

In another example of the present invention, a content of the styrene-isoprene-styrene block copolymer in the mixture of a styrene-isoprene-styrene block copolymer and a styrene-isoprene copolymer is preferably 50% by weight or more and 95% by weight or less, more preferably 60% by weight or more and 95% by weight or less, and most preferably 70% by weight or more and 90% by weight or less.

A content of styrene in a styrene-isoprene-styrene block copolymer and a styrene-isoprene copolymer is not particularly limited. The lower limit of the content of styrene is preferably 5% by weight or more, and particularly preferably 10% by weight or more. The upper limit of the content of styrene is preferably 50% by weight or less, more preferably 30% by weight or less, and most preferably 20% by weight or less.

In the above-described ranges, a content of styrene in a styrene-isoprene-styrene block copolymer and a styrene-isoprene copolymer is preferably 5% by weight or more and 50% by weight or less, more preferably 10% by weight or more and 30% by weight or less, and most preferably 10% by weight or more and 20% by weight or less.

The styrene-isoprene-styrene block copolymer and the styrene-isoprene block copolymer can each be a copolymer produced by a known method. Otherwise, commercially available products, which meet the above-described properties, can also be used. In addition, such a mixture of a styrene-isoprene-styrene block copolymer and a styrene-isoprene block copolymer is commercially available, and examples of the commercially available product include "KRATON D1161," "KRATON D1163," "KRATON D1113" and "KRATON D1119," which are manufactured by KRATON POLYMERS, "JSR 5229," "JSR 5403" and "JSR 5505," which are manufactured by JSR, and "Quintac 3620" "Quintac 3421" and "Quintac 3520," which are manufactured by Zeon Corporation.

A content of the rubber-based pressure-sensitive adhesive is not particularly limited, as long as it is in the range that does not impair sufficient drug release properties, cohesiveness and adhesiveness, which are the objects of the present invention. In one example of the present invention, the lower limit of the content of the rubber-based pressure-sensitive adhesive is preferably 15% by weight or more, more preferably 25% by weight or more, particularly preferably 30% by weight or more, and most preferably 35% by weight or more, based on the total amount of pressure-sensitive adhesive components. On the other hand, the upper limit of the content of the rubber-based pressure-sensitive adhesive is preferably 60% by weight or less, more preferably 55% by weight or less, and most preferably 50% by weight or less, based on the total amount of pressure-sensitive adhesive components.

In one example of the present invention, in the above-described ranges, a content of the rubber-based pressure-sensitive adhesive is preferably 30% by weight or more and 55% by weight or less, and more preferably 35% by weight or more and 50% by weight or less.

(c) Liquid Paraffin

The liquid paraffin that can be used in the present invention is not particularly limited. Commercially available liquid paraffin can be preferably used.

A content of the liquid paraffin used in the present invention is not particularly limited, as long as it is in the range that does not impair the effects of the present invention, such as the adhesiveness and drug release properties of the pressure-sensitive adhesive. The lower limit of the content of the liquid paraffin is preferably 0.5 times by weight or more, based on a weight of the rubber-based pressure-sensitive adhesive. It may be 0.6 times by weight or more, or 0.7 times by weight or more, or 0.8 times by weight or more, or 0.9 times by weight or more, or 1.0 time by weight or more, or 1.5 times by weight or more, or 2.0 times by weight or more, or 2.3 times by weight or more, or 2.6 times by weight or more. On the other hand, the upper limit of the content of the liquid paraffin is preferably 7.0 times by weight or less, based on a weight of the rubber-based pressure-sensitive adhesive. It may be 6.0 times by weight or less, or 5.5 times by weight or less, or 5.0 times by weight or less, or 3.0 times by weight or less, or 2.6 times by weight or less, or 2.0 times by weight or less, or 1.7 times by weight or less, or 1.6 times by weight or less, or 1.5 times by weight or less.

In one example, a content of the liquid paraffin is preferably 0.5 times by weight or more and 2.6 times by weight or less, more preferably 0.6 times by weight or more and 2.0 times by weight or less, further preferably 0.7 times by weight or more and 1.7 times by weight or less, particularly preferably 0.7 times by weight or more and 1.6 times by weight or less, and most preferably 0.7 times by weight or more and 1.5 times by weight or less, based on a weight of the rubber-based pressure-sensitive adhesive.

In another example, a content of the liquid paraffin is preferably 2.0 times by weight or more and 6.0 times by weight or less, more preferably 2.3 times by weight or more and 5.5 times by weight or less, and further preferably 2.6 times by weight or more and 5.0 times by weight or less, based on a weight of the rubber-based pressure-sensitive adhesive.

In one example of the present invention, the lower limit of the content of the liquid paraffin is preferably 30% by weight or more, more preferably 35% by weight or more, and most preferably 40% by weight or more, based on the total amount of pressure-sensitive adhesive components. On the other hand, the upper limit of the content of the liquid paraffin is preferably 70% by weight or less, more preferably 65% by weight or less, particularly preferably 60% by weight or less, and most preferably 55% by weight or less, based on the total amount of pressure-sensitive adhesive components.

In one example of the present invention, in the above-described ranges, a content of the liquid paraffin is preferably 30% by weight or more and 65% by weight or less, more preferably 35% by weight or more and 60% by weight or less, and most preferably 40% by weight or more and 55% by weight or less, based on the total amount of pressure-sensitive adhesive components.

Moreover, when the rubber-based pressure-sensitive adhesive is a mixture of a styrene-isoprene-styrene block copolymer and a styrene-isoprene block copolymer, if a weight of the liquid paraffin to a weight of the rubber-based pressure-sensitive adhesive is defined as y, a weight percent of the styrene-isoprene-styrene copolymer in the mixture of a styrene-isoprene-styrene block copolymer and a styrene-isoprene block copolymer is defined as x, and the base of natural logarithm is defined as e, the patch of the present invention satisfies preferably the following exponential: $0.48e^{0.022x}-0.4 \leq y \leq e^{0.021x}+0.4$, more preferably the following exponential: $0.48e^{0.022x}-0.2 \leq y \leq e^{0.021x}+0.2$, and further preferably the following exponential: $0.48e^{0.022x} \leq y \leq e^{0.021x}$.

It is noted that the patches of the after-mentioned Examples 1 to 17 satisfy the exponential: $0.48e^{0.022x} \leq y \leq e^{0.021x}$.

(d) Tackifier

A tackifier may be added into the above-described pressure-sensitive adhesive layer. The term "tackifier" is used herein to mean a tackifier that is commonly used in the field of patches, and examples of such a tackifier include a rosin resin, a polyterpene resin, a coumarone-indene resin, a petroleum resin, a terpene-phenol resin, and an alicyclic saturated hydrocarbon resin. If a large amount of tackifier is added into the pressure-sensitive adhesive layer, the drug-releasing property is reduced. Accordingly, a content of the tackifier is preferably 10% by weight or less, more preferably 5% by weight or less, and most preferably no tackifiers contained, based on the total amount of pressure-sensitive adhesive components.

(e) Other Components

The patch of the present invention can comprise (e1) a surfactant, (e2) esters, (e3) alcohols, (e4) an antioxidant, (e5) a filler, etc., as necessary.

(e1) Surfactant

Examples of the surfactant include a nonionic surfactant, an anionic surfactant, a cationic surfactant, and an amphoteric surfactant.

Examples of the nonionic surfactant include sorbitan monolaurate, sorbitan monopalmitate, sorbitan sesquioleate, glycerol monooleate, glycerol monostearate, decaglyceryl monolaurate, hexaglycerin polyricinoleate, polyoxyethylene (9) lauryl ether, polyoxyethylene (2) lauryl ether, polyoxyethylene (4,2) lauryl ether, polyoxyethylene (5) nonyl phenyl ether, polyoxyethylene (7,5) nonyl phenyl ether, polyoxyethylene (10) nonyl phenyl ether, polyoxyethylene (3) octyl phenyl ether, polyoxyethylene (10) octyl phenyl ether, polyoxyethylene (10) oleylamine, polyoxy (5) oleylamine, polyoxy (5) oleic amide, polyoxyethylene (2) monolaurate, monoglyceride stearate, and polyoxyethylene castor oil (hydrogenated castor oil).

Examples of the anionic surfactant include sodium lauryl sulfate, potassium lauryl sulfate, triethanolamine lauryl sulfate, sodium cetyl sulfate, sodium lauroylsarcosinate, di-2-ethylhexyl sodium sulfosuccinate, polyoxyethylene (10) lauryl ether sodium phosphate, polyoxyethylene (4) lauryl ether sodium phosphate, polyoxyethylene (5) cetyl ether sodium phosphate, and polyoxyethylene (6) oleyl ether sodium phosphate.

Examples of the cationic surfactant include stearyltrimethylammonium chloride, distearyldimethylammonium chloride, benzalkonium chloride, and stearyldimethylbenzylammonium chloride.

Examples of the amphoteric surfactant include lauryldimethylaminoacetic acid betaine and 2-alkyl-N-carboxymethyl-N-hydroxyethyl imidazolinium betaine. In addition to the above-described substances, lauroyl diethanol amide can also be used. Among others, nonionic surfactants are preferable, and sorbitan monolaurate, sorbitan monopalmitate, sorbitan sesquioleate, glycerol monooleate, and glycerol monostearate are more preferable.

The surfactants may be used alone, or in combination of two or more types.

A content of the surfactant is not particularly limited. The surfactant can be comprised in the patch of the present invention to such an extent that the present patch can maintain high skin permeability, and cohesive force and adhesive force patch that are sufficient for the patch. A content of the surfactant is preferably 5% by weight or less, and more preferably 3% by weight or less, based on the total amount of pressure-sensitive adhesive components.

When the surfactant is used, it can be added to the patch of the present invention by being replaced with the rubber-based pressure-sensitive adhesive and/or liquid paraffin that constitute the pressure-sensitive adhesive layer.

(e2) Esters

Examples of the esters used herein include: esters of fatty acid and monohydric alcohol such as isopropyl isostearate, methyl stearate, butyl stearate, butyl myristate, ethyl linoleate, isopropyl linoleate, ethyl oliveoleate, myristyl myristate, cetyl isooctanoate, octyldodecyl myristate, diisopropyl adipate, cetyl palmitate, retinol palmitate, methyl laurate, methyl myristate, methyl caproate, methyl palmitate, isopropyl myristate, isopropyl palmitate, diethyl sebacate, or diethyl adipate; esters of fatty acid and polyhydric alcohol such as glycerin monooleate, glycerin monocaprate, glycerin dioleate, propylene glycol monostearate, or decaglycerin decaoleate; esters of fatty acid and cyclic polyhydric alcohol such as sorbitan monostearate, sorbitan monolaurate, sorbitan monooleate, sorbitan trioleate, or ascorbyl palmitate; lactate such as cetyl lactate or myristyl lactate; carbonate such as propylene carbonate; and pyrrolidone derivatives such as N-methyl-2-pyrrolidone.

The esters may be used alone, or in combination of two or more types.

A content of the esters is not particularly limited, and the esters can be comprised in the patch of the present invention to such an extent that the present patch can maintain high skin permeability, and cohesive force and adhesive force patch that are sufficient for the patch. Among others, a content of the esters is preferably 55% by weight or less, more preferably 45% by weight or less, further preferably 35% by weight or less, particularly preferably 25% by weight or less, and most preferably 15% by weight or less, based on the total amount of pressure-sensitive adhesive components.

When the esters are used, they can be added to the patch of the present invention by being replaced with the rubber-based pressure-sensitive adhesive and/or liquid paraffin that constitute the pressure-sensitive adhesive layer. From the viewpoint of ensuring the cohesiveness of a formulation, the esters are preferably replaced with liquid paraffin. The entire liquid paraffin may be replaced with the esters, or a part thereof may be replaced with the esters.

(e3) Alcohols

Examples of the alcohols include: aliphatic alcohols such as ethanol, isopropanol, lauryl alcohol, 2-octyl dodecanol, 2-hexyl decanol, ethylene glycol, propylene glycol, 1,3-butanediol, or glycerin; and aromatic alcohols such as glycol salicylate or benzyl alcohol. The alcohols are preferably aliphatic alcohols, and more preferably lauryl alcohol, 2-octyl dodecanol, 2-hexyl decanol, propylene glycol, 1,3-butanediol, etc. The alcohols may be used alone, or in combination of two or more types.

A content of the alcohols is not particularly limited, and the alcohols can be comprised in the patch of the present invention to such an extent that the present patch can maintain high skin permeability, and cohesive force and adhesive force patch that are sufficient for the patch. Among others, a content of the alcohols is preferably 55% by weight or less, more preferably 45% by weight or less, further preferably 35% by weight or less, particularly preferably 25% by weight or less, and most preferably 15% by weight or less, based on the total amount of pressure-sensitive adhesive components.

When the alcohols are used, they can be added to the patch of the present invention by being replaced with the rubber-based pressure-sensitive adhesive and/or liquid paraffin that constitute the pressure-sensitive adhesive layer. From the viewpoint of ensuring the cohesiveness of a formulation, the alcohols are preferably replaced with liquid paraffin. The entire liquid paraffin may be replaced with the alcohols, or a part thereof may be replaced with the alcohols.

(e4) Antioxidant

Examples of the antioxidant used herein include dibutyl hydroxyl toluene, 4-dioxyphenol, and EDTA-2Na. Among others, dibutyl hydroxyl toluene is preferable. The antioxidants may be used alone, or in combination of two or more types.

A content of the antioxidant is not particularly limited, and the antioxidant can be comprised in the patch of the present invention to such an extent that the present patch can maintain high skin permeability, and cohesive force and adhesive force patch that are sufficient for the patch. Among others, a content of the antioxidant is preferably 10% by weight or less, more preferably 5% by weight or less, and most preferably 2% by weight or less, based on the total amount of pressure-sensitive adhesive components.

When the antioxidant is used, it can be added to the patch of the present invention by being replaced with the rubber-based pressure-sensitive adhesive and/or liquid paraffin that constitute the pressure-sensitive adhesive.

(e5) Filler

In order to regulate the flexibility of the pressure-sensitive adhesive layer, the patch of the present invention can comprise a filler.

Examples of the filler include kaolin, titanium oxide, talc, calcium carbonate, magnesium carbonate, silicate, silicic acid, aluminum hydrate, barium sulfate, and calcium sulfate. The fillers may be used alone, or in combination of two or more types.

A content of the filler is not particularly limited, and the filler can be comprised in the patch of the present invention to such an extent that the present patch can maintain high skin permeability, and cohesive force and adhesive force patch that are sufficient for the patch. Among others, a content of the filler is preferably 10% by weight or less, more preferably 5% by weight or less, and most preferably 2% by weight or less, based on the total amount of pressure-sensitive adhesive components.

When the filler is used, it can be added to the patch of the present invention by being replaced with the rubber-based pressure-sensitive adhesive and/or liquid paraffin that constitute the pressure-sensitive adhesive.

[Backing]

The backing used in the present invention is not particularly limited, and a commonly used backing can be used herein. Examples of such a backing include: plastic films such as a polyester film, a polyethylene film, a polypropylene film, a polyvinyl chloride film, a polycarbonate film, a polyurethane film, and a cellophane film; foams; fabric base materials, for example, non-woven fabrics, woven fabrics and knitted fabrics, such as those comprising a polyester fiber, a polyethylene fiber, a polypropylene fiber, etc.; and laminates thereof. Among these materials, a backing formed with a material comprising polyester is preferable. From the viewpoint of elasticity, a non-woven fabric, a woven fabric and a knitted fabric are preferable, and also, from the viewpoint of usability, a film having transparency is preferable.

[Method of Preparing Pressure-Sensitive Adhesive Composition Used in Production of Patch]

The patch of the present invention can be prepared using the below-mentioned pressure-sensitive adhesive composition. The pressure-sensitive adhesive composition can be prepared by mixing and stirring pressure-sensitive adhesive components. Specifically, (a) lidocaine and another local anesthetic, (b) a rubber-based pressure-sensitive adhesive, and (c) liquid paraffin are mixed and stirred, so as to obtain a pressure-sensitive adhesive composition. With regard to the order of mixing the aforementioned components, for example, the above-described components from (a) to (c) may be successively added, or it may also be possible that the above-described component (b) and the above-described component (c) have previously been mixed with each other and that the above-described component (a) is then mixed with the mixture.

During the mixing and stirring operations, it is preferable to heat the components because the components are easily homogeneously mixed under heating. The heating temperature is preferably 50° C. or higher, more preferably 70° C. or higher, and most preferably 90° C. or higher. In order to prevent degeneration or volatilization of the components of the pressure-sensitive adhesive composition, the upper limit of the temperature is preferably 170° C. or lower, and more preferably 150° C. or lower.

In the above-described ranges, the heating temperature is preferably 40° C. or higher and 170° C. or lower, more preferably 70° C. or higher and 170° C. or lower, particularly preferably 70° C. or higher and 150° C. or lower, and most preferably 90° C. or higher and 150° C. or lower.

Moreover, it is also possible to further add a solvent to the pressure-sensitive adhesive components to prepare a pressure-sensitive adhesive solution, which can be then used in the production of a patch.

The solvent used in the present invention is not particularly limited, as long as it is a solvent capable of dissolving the pressure-sensitive adhesive components. For example, organic solvents such as toluene, hexane, heptane, ethyl acetate, isopropyl acetate, n-propyl acetate and N-methyl-2-pyrrolidone can be preferably used. From the viewpoint of dissolving property and easy dryness, toluene, hexane, heptane, ethyl acetate and isopropyl acetate can be preferably used, and among these, toluene is particularly preferable.

When a solvent is used during the mixing and stirring operations, the components can be homogeneously mixed without particular heating. In order to homogeneously and quickly mix the components, the components may also be heated. The heating temperature is preferably 30° C. or higher, and more preferably 40° C. or higher. If the heating temperature is too high, the solvent is easily volatilized. Thus, the heating temperature is preferably 120° C. or lower, more preferably 100° C. or lower, and most preferably 90° C. or lower.

In the above-described ranges, the heating temperature is preferably 30° C. or higher and 120° C. or lower, more preferably 40° C. or higher and 100° C. or lower, and most preferably 40° C. or higher and 90° C. or lower.

[Method for Producing Patch]

As a method for producing the patch of the present invention, a method comprising coating to a backing with a pressure-sensitive adhesive layer can be preferably applied.

As a method for producing the patch of the present invention, a method similar to a method for producing an adhesive tape can be adopted. Examples of such a method include a hot melt coating method which comprises heating and melting a pressure-sensitive adhesive composition and then coating to a backing with the melted pressure-sensitive adhesive composition, and a solvent coating method which comprises dissolving a pressure-sensitive adhesive composition in an organic solvent, then coating a backing with the obtained pressure-sensitive adhesive solution, and then drying it.

In addition, as other methods for producing the patch of the present invention, there can also be applied a method which comprises once applying a pressure-sensitive adhesive composition onto a release paper, then peeling the composition from the release paper, and then transcribing and hermetically adhering to a backing, or a method which comprises transcribing a coated surface on a backing and hermetically adhering it thereto, without peeling the composition from the release paper.

Such a release paper is used for the purpose of protecting the pressure-sensitive adhesive layer. Taking into consideration its easy peeling property from the pressure-sensitive adhesive layer, breathability, water permeability, flexibility and the like, the release paper can be selected, as appropriate, depending on purpose. As such a release paper, a film comprising a polymeric material such as polyethylene, polypropylene or polyester is preferably used, and in order to enhance its peeling property, the surface of such a film can be subjected to a silicone treatment or a fluorocarbon treatment, and can be then used.

In the patch of the present invention, the pressure-sensitive adhesive layer may be a single layer or multiple layers consisting of two or more layers. When the pressure-sensitive adhesive layer consists of multiple layers, it may be adequate if at least one layer thereof comprises a mixture of lidocaine and another local anesthetic.

In the patch of the present invention, the thickness of the pressure-sensitive adhesive layer is preferably 20 μm or more and 2000 μm or less, more preferably 50 μm or more and 1500 μm or less, particularly preferably 100 μm or more and 1000 μm or less, and most preferably 120 μm or more and 600 μm or less.

[Intended Use of Patch]

The patch of the present invention can be used as a transdermal absorption preparation.

Since the patch of the present invention comprises lidocaine and another local anesthetic, it can be used as a local anesthetic agent.

Moreover, since the patch of the present invention comprises lidocaine and another local anesthetic, it can also be used as an analgesic or a pain therapeutic agent, can be preferably used as a therapeutic agent for neuropathic pain, and can be used, for example, as a therapeutic agent for postherpetic neuralgia.

EXAMPLES

Hereinafter, the present invention will be more specifically described in the following examples and test examples. However, these examples are not intended to limit the scope of the present invention. It is to be noted that the numerical value of each component shown in Table 1 to Table 9 indicates part by mass.

(Evaluation Method) Evaluation of Skin Permeability

A skin, which had been extracted from the abdomen of a hair-removed male Wister rat (5 weeks old), was set on a vertical Franz diffusion cell (manufactured by Vidrex Co., Ltd., model number: TP-8s). A patch, which had been produced in each of Examples and Comparative Examples, was punced out in a circle shape with a diameter of 1.3 cm, and it was then attached onto the rat skin on the Franz diffusion cell. Using a 5% ethanol-containing 0.01 mol/L phosphate buffered saline (pH 7.2 to 7.4) as a buffer, a test was carried out at a buffer temperature of 32° C. One hour after initiation of the test, an aliquot was took from the buffer, and the amount of lidocaine and the amount of prilocaine in the buffer, which had been permeated through the rat skin, were quantified by HPLC. The sum of the permeated amounts of lidocaine and prilocaine was defined as a drug permeation amount, and the magnification of the present drug permeation amount to the drug permeation amount obtained in the case of using the existing lidocaine patch (manufactured by YUTOKU PHARMACEUTICAL IND. Co., Ltd.; product name: Youpatch(Registered trademark) Tape) was evaluated.

(Evaluation Method) Cohesive Force

The cohesive force of the patch was evaluated from the following viewpoints.

○: No adhesive deposit was observed.
Δ: Although cohesive force was slightly insufficient, it did not cause particular problems.
x: Adhesive deposit, deformation and the like were observed, and cohesive force was significantly insufficient.

(Evaluation Method) Adhesiveness

The adhesiveness of the patch was evaluated from the following viewpoints.

○: The patch exhibited higher adhesiveness than the existing local anesthetic patch (lidocaine tape agent).
Δ: The patch exhibited slightly lower adhesiveness than the existing local anesthetic patch (lidocaine tape agent).
x: Significant peeling off was observed.

Example 1

9.45 g of toluene was added to 5.40 g of a mixture of a styrene-isoprene-styrene block copolymer and a styrene-isoprene copolymer (the weight mixing ratio of the styrene-isoprene-styrene block copolymer/the styrene-isoprene copolymer=50/50) and 8.10 g of liquid paraffin, and these components were then mixed. Thereafter, the mixture was stirred under heating at an internal temperature of 50° C. for 120 minutes, so that the components were completely dissolved. After that, the mixture was cooled to 20° C.-30° C. Subsequently, 0.75 g of lidocaine and 0.75 g of prilocaine were successively added to the mixture, and the obtained mixture was mixed and stirred at the same temperature as described above for 15 hours or more, so as to obtain a homogeneous pressure-sensitive adhesive solution. Using an applicator, the pressure-sensitive adhesive solution was coated onto a polyethylene terephthalate (PET) film with a thickness of 80 μm, the surface of which had been treated with silicone, and thereafter, toluene was removed therefrom by drying it in a hot air oven at 60° C. for 120 minutes or more, so as to form a pressure-sensitive adhesive layer having a thickness after drying of 350 to 450 μm. Thereafter, a PET film with a thickness of 60 μm was laminated on the surface of the pressure-sensitive adhesive layer, thereby producing a patch of interest (transdermal absorption formulation). The components of the pressure-sensitive adhesive and the weight ratio (%) thereof are shown in Table 1.

Examples 2 and 3

A patch was produced by the same method as that applied in Example 1, with the exception that lidocaine, prilocaine, an SIS copolymer and liquid paraffin were mixed at the ratios shown in Table 1.

Example 4

2.24 g of toluene was added to 1.60 g of a mixture of a styrene-isoprene-styrene block copolymer and a styrene-isoprene copolymer (the weight mixing ratio of the styrene-isoprene-styrene block copolymer/the styrene-isoprene copolymer=50/50) and 1.60 g of liquid paraffin, and these components were then mixed. Thereafter, the mixture was stirred under heating at an internal temperature of 50° C. for 120 minutes, so that the components were completely dissolved in the toluene. After that, the mixture was cooled to 20° C.-30° C. Subsequently, 0.40 g of a tackifier, 0.20 g of lidocaine, and 0.20 g of prilocaine were successively added to the mixture, and the obtained mixture was mixed and stirred at the same temperature as described above for 15 hours or more, so as to obtain a homogeneous pressure-sensitive adhesive solution. Using an applicator, the pressure-sensitive adhesive solution was coated onto a polyethylene terephthalate (PET) film with a thickness of 80 μm, the surface of which had been treated with silicone, and thereafter, toluene was removed therefrom by drying it in a hot air oven at 60° C. for 120 minutes or more, so as to form a pressure-sensitive adhesive layer having a thickness after drying of 350 to 450 μm. Thereafter, a PET film with a thickness of 60 μm was laminated on the surface of the pressure-sensitive adhesive layer, thereby producing a patch of interest. The components of the pressure-sensitive adhesive and the weight ratio (%) thereof are shown in Table 1. (SIS)

SIS-A: Weight mixing ratio of styrene-isoprene-styrene block copolymer/styrene-isoprene copolymer=80/20
SIS-B: Weight mixing ratio of styrene-isoprene-styrene block copolymer/styrene-isoprene copolymer=50/50
SIS-C: Weight mixing ratio of styrene-isoprene-styrene block copolymer/styrene-isoprene copolymer=22/78
SIS-D: Weight mixing ratio of styrene-isoprene-styrene block copolymer/styrene-isoprene copolymer=88/12
SIS-E: Weight mixing ratio of styrene-isoprene-styrene block copolymer/styrene-isoprene copolymer=74/26

TABLE 1

|  |  | Example 1 | Example 2 | Example 3 | Example 4 |
|---|---|---|---|---|---|
| Active pharmaceutical ingredient | Lidocaine | 5 | 5 | 2.5 | 5 |
|  | Prilocaine | 5 | 5 | 2.5 | 5 |
| Tackifier | Alicyclic saturated hydrocarbon resin |  |  |  | 10 |
|  | Rosin ester |  |  |  |  |
| SIS | SIS A |  |  |  |  |
|  | SIS B | 36 |  |  | 40 |
|  | SIS C |  | 45 | 47.5 |  |
| Liquid paraffin |  | 54 | 45 | 47.5 | 40 |
| Acrylic pressure-sensitive adhesive |  |  |  |  |  |
| Cohesive force |  | ○ | ○ | ○ | ○ |
| Adhesiveness |  | ○ | ○ | ○ | ○ |
| Skin permeability |  | 6.0 times higher | 8.6 times higher | 3.4 times higher | 3.5 times higher |

The patches of Examples 1 to 4 all exhibited good cohesive force and adhesiveness. In addition, the skin permeability of the patch of each of Examples 1 to 4 was extremely higher than that of the existing lidocaine tape agent (3.4 to 8.6 times higher than the existing agent).

Comparative Examples 1 to 6

A patch was produced by the same method as that applied in Example 1, with the exception that lidocaine, an SIS copolymer and liquid paraffin were mixed at the ratios shown in Table 2.

TABLE 2

|  |  | Comp. Ex. 1 | Comp. Ex. 2 | Comp. Ex. 3 | Comp. Ex. 4 | Comp. Ex. 5 | Comp. Ex. 6 |
|---|---|---|---|---|---|---|---|
| Active pharmaceutical ingredient | Lidocaine | 10 | 10 |  |  | 5 | 5 |
|  | Prilocaine |  |  | 10 | 10 |  |  |
| Tackifier | Alicyclic saturated hydrocarbon resin |  |  |  |  |  |  |
|  | Rosin ester |  |  |  |  |  |  |
| SIS | SIS A |  |  |  |  | 28 |  |
|  | SIS B | 36 |  | 36 |  |  | 12 |
|  | SIS C |  | 45 |  | 45 |  |  |
| Acrylic pressure-sensitive adhesive |  |  |  |  |  |  |  |
| Liquid paraffin |  | 54 | 45 | 54 | 45 | 67 | 78 |
| Propylene glycol |  |  |  |  |  |  | 1 |
| Polyethylene glycol 400 |  |  |  |  |  |  | 4 |
| Cohesive force |  | ○ | ○ | Δ | Δ | ○ | Δ |
| Adhesiveness |  | x | x | x | x | Δ | x |
| Skin permeability |  | — | — | — | — | even | — |

When lidocaine alone or prilocaine alone was formulated as a drug, the patches of Comparative Examples 1 to 6 had low adhesiveness, and thus, the patches have not reached practical levels of pharmaceutical products.

Comparative Examples 7 and 8

A patch was produced by the same method as that applied in Example 4, with the exception that lidocaine, prilocaine, an SIS copolymer and liquid paraffin were mixed at the ratios shown in Table 3.

TABLE 3

|  |  | Comp. Ex. 7 | Comp. Ex. 8 |
|---|---|---|---|
| Active pharmaceutical ingredient | Lidocaine | 5 | 5 |
|  | Prilocaine | 5 | 5 |
| Tackifier | Alicyclic saturated hydrocarbon resin | 35 |  |
|  | Rosin ester |  | 35 |
| SIS | SIS A | 27 | 27 |
|  | SIS B |  |  |
|  | SIS C |  |  |

TABLE 3-continued

|  | Comp. Ex. 7 | Comp. Ex. 8 |
|---|---|---|
| Liquid paraffin | 28 | 28 |
| Acrylic pressure-sensitive adhesive |  |  |
| Cohesive force | ○ | ○ |
| Adhesiveness | ○ | ○ |
| Skin permeability | 1.5 times higher | 2.0 times higher |

Although the patches of Comparative Examples 7 and 8 had extremely good adhesive force and cohesive force as a result of the addition of the tackifier, they had insufficient skin permeability of drug, in comparison to the patches of Examples 1 to 4.

Comparative Example 9

0.20 g of lidocaine and 0.20 g of prilocaine were successively added to 7.76 g of a crosslinked acrylic-base copolymer (Durotak 87-901 A, 44 wt % solution), and the obtained mixture was then mixed and stirred at room temperature for 15 hours, so as to obtain a homogeneous pressure-sensitive adhesive solution. Using an applicator, the pressure-sensitive adhesive solution was coated onto a polyethylene terephthalate (PET) film with a thickness of 80 µm, the surface of which had been treated with silicone, and thereafter, toluene was removed therefrom by drying it in a hot air oven at 60° C. for 120 minutes or more, so as to form a pressure-sensitive adhesive layer having a thickness after drying of 350 to 450 µm. Thereafter, a PET film with a thickness of 60 µm was laminated on the surface of the pressure-sensitive adhesive layer, thereby producing a patch of interest. The components of the pressure-sensitive adhesive and the weight ratio (%) thereof are shown in Table 4.

TABLE 4

| | | Comp. Ex. 9 |
|---|---|---|
| Active pharmaceutical ingredient | Lidocaine | 5 |
| | Prilocaine | 5 |
| Tackifier | Alicyclic saturated hydrocarbon resin | |
| | Rosin ester | |
| SIS | SIS A | |
| | SIS B | |
| | SIS C | |
| Liquid paraffin | | |
| Acrylic pressure-sensitive adhesive | | 90 |
| Cohesive force | | ○ |
| Adhesiveness | | ○ |
| Skin permeability | | 2.2 times higher |

Although the patch of Comparative Example 9, in which an acrylic-base adhesive base preparation was used, had good cohesive force and adhesive force, it had significantly decreased skin permeability in comparison to the patches of Examples 1 to 4.

Examples 5 and 6

A patch was produced by the same method as that applied in Example 1, with the exception that lidocaine, prilocaine, an SIS copolymer and liquid paraffin were mixed, with the types and at the ratios shown in Table 5.

TABLE 5

| | | Example 5 | Example 6 |
|---|---|---|---|
| Active pharmaceutical ingredient | Lidocaine | 6 | 7.5 |
| | Prilocaine | 6 | 7.5 |
| Tackifier | Alicyclic saturated hydrocarbon resin | | |
| | Rosin ester | | |
| SIS | SIS A | | |
| | SIS B | | |
| | SIS C | 44 | 42.5 |
| | SIS D | | |
| | SIS E | | |
| Liquid paraffin | | 44 | 42.5 |
| Acrylic pressure-sensitive adhesive | | | |
| Cohesive force | | Δ to ○ | Δ to ○ |
| Adhesiveness | | ○ | ○ |
| Skin permeability | | 6.4 times higher | 5.9 times higher |

The patches of Examples 5 and 6, in which the concentration of the drug was changed, exhibited cohesive force and adhesiveness causing no practical problems, and also had sufficiently high skin permeability.

Examples 7 to 17

A patch was produced by the same method as that applied in Example 1, with the exception that lidocaine, prilocaine, an SIS copolymer and liquid paraffin were mixed, with the types and at the ratios shown in Table 6.

TABLE 6

| | | Example 7 | Example 8 | Example 9 | Example 10 | Example 11 | Example 12 |
|---|---|---|---|---|---|---|---|
| Active pharmaceutical ingredient | Lidocaine | 5 | 5 | 5 | 5 | 5 | 5 |
| | Prilocaine | 5 | 5 | 5 | 5 | 5 | 5 |
| Tackifier | Alicyclic saturated hydrocarbon resin | | | | | | |
| | Rosin ester | | | | | | |
| SIS | SIS A | 20 | 15 | | | | |
| | SIS B | | | 35 | 30 | 25 | |
| | SIS C | | | | | | 50 |
| | SIS D | | | | | | |
| | SIS E | | | | | | |
| Liquid paraffin | | 70 | 75 | 55 | 60 | 65 | 40 |
| Acrylic pressure-sensitive adhesive | | | | | | | |
| Cohesive force | | ○ | ○ | ○ | ○ | Δ to ○ | ○ |
| Adhesiveness | | Δ to ○ | Δ to ○ | Δ to ○ | Δ to ○ | Δ to ○ | Δ to ○ |

TABLE 6-continued

| Skin permeability | 16 times higher | 6.6 times higher | 4.2 times higher | — | 3.4 times higher | 9.0 times higher |
|---|---|---|---|---|---|---|
| Ratio of liquid paraffin to rubber-based pressure-sensitive adhesive | 3.5 | 5 | 1.57 | 2 | 2.6 | 0.8 |

| | | Example 13 | Example 14 | Example 15 | Example 16 | Example 17 |
|---|---|---|---|---|---|---|
| Active pharmaceutical ingredient | Lidocaine | 5 | 5 | 5 | 5 | 5 |
| | Prilocaine | 5 | 5 | 5 | 5 | 5 |
| Tackifier | Alicyclic saturated hydrocarbon resin | | | | | |
| | Rosin ester | | | | | |
| SIS | SIS A | | | | | |
| | SIS B | | | | | |
| | SIS C | 40 | 35 | | | |
| | SIS D | | | 20 | | |
| | SIS E | | | | 25 | 20 |
| Liquid paraffin | | 50 | 55 | 70 | 65 | 70 |
| Acrylic pressure-sensitive adhesive | | | | | | |
| Cohesive force | | ○ | ○ | Δ to ○ | ○ | ○ |
| Adhesiveness | | ○ | ○ | Δ to ○ | Δ to ○ | Δ to ○ |
| Skin permeability | | 8.1 times higher | — | 12 times higher | 7.6 times higher | 3.5 times higher |
| Ratio of liquid paraffin to rubber-based pressure-sensitive adhesive | | 1.25 | 1.57 | 3.5 | 2.6 | 3.5 |

The patches of Examples 7 to 17, in which the ratio between the liquid paraffin and the SIS copolymer and the type of the SIS copolymer were changed, exhibited cohesive force and adhesiveness causing no practical problems, and also had sufficiently high skin permeability.

Examples 18 and 19

A patch was produced by the same method as that applied in Example 1, with the exception that lidocaine, prilocaine, an SIS copolymer and liquid paraffin were mixed, with the types and at the ratios shown in Table 7.

TABLE 7

| | | Example 18 | Example 19 |
|---|---|---|---|
| Active pharmaceutical ingredient | Lidocaine | 5 | 5 |
| | Prilocaine | 5 | 5 |
| Tackifier | Alicyclic saturated hydrocarbon resin | | |
| | Rosin ester | | |
| SIS | SIS A | 30 | 25 |
| | SIS B | | |
| | SIS C | | |
| | SIS D | | |
| | SIS E | | |
| Liquid paraffin | | 60 | 65 |
| Acrylic pressure-sensitive adhesive | | | |
| Cohesive force | | ○ | ○ |
| Adhesiveness | | Δ | Δ |
| Skin permeability | | 7.9 times higher | 8.7 times higher |
| Ratio of liquid paraffin to rubber-based pressure-sensitive adhesive | | 2 | 2.6 |

The patches of Examples 18 and 19, in which the ratio between the liquid paraffin and the SIS copolymer and the type of the SIS copolymer were changed, exhibited cohesive force and adhesiveness causing no practical problems, and also had sufficiently high skin permeability.

Examples 20 and 21

A patch was produced by the same method as that applied in Example 1, with the exception that active pharmaceutical ingredients, an SIS copolymer and liquid paraffin were mixed, with the types and at the ratios shown in Table 8.

TABLE 8

| | | Example 20 | Example 21 |
|---|---|---|---|
| Active pharmaceutical ingredient | Lidocaine | 3.5 | 2.5 |
| | Benzocaine | 1.5 | |
| | Tetracaine | | 2.5 |
| Tackifier | Alicyclic saturated hydrocarbon resin | | |
| | Rosin ester | | |
| SIS | SIS A | | |
| | SIS B | | |
| | SIS C | 47.5 | 47.5 |
| | SIS D | | |
| | SIS E | | |
| Liquid paraffin | | 47.5 | 47.5 |
| Acrylic pressure-sensitive adhesive | | | |
| Cohesive force | | ○ | ○ |
| Adhesiveness | | Δ to ○ | ○ |
| Skin permeability | | 7.0 times higher | 4.4 times higher |

The patches of Examples 20 and 21, in which the types of the active pharmaceutical ingredients were changed, exhibited cohesive force and adhesiveness causing no practical problems, and also had sufficiently high skin permeability.

Examples 22 and 23

A patch was produced by the same method as that applied in Example 1, with the exception that active pharmaceutical ingredients, an SIS copolymer and liquid paraffin were mixed, with the types and at the ratios shown in Table 9.

TABLE 9

|  |  | Example 22 | Example 23 |
|---|---|---|---|
| Active pharmaceutical ingredient | Lidocaine | 4 | 6 |
|  | Prilocaine | 6 | 4 |
| Tackifier | Alicyclic saturated hydrocarbon resin |  |  |
|  | Rosin ester |  |  |
| SIS | SIS A |  |  |
|  | SIS B |  |  |
|  | SIS C | 45 | 45 |
|  | SIS D |  |  |
|  | SIS E |  |  |
| Liquid paraffin |  | 45 | 45 |
| Acrylic pressure-sensitive adhesive |  |  |  |
| Cohesive force |  | ○ | ○ |
| Adhesiveness |  | ○ | ○ |
| Skin permeability |  | 9.1 times higher | 6.8 times higher |

The patches of Examples 22 and 23, in which the mixing ratio of the active pharmaceutical ingredients was changed, exhibited good cohesive force and adhesiveness, and also had sufficient skin permeability.

[Concerning Pain Relief or Pain Treatment Effects]

Test Example 1

Evaluation of In Vitro Rat Skin Permeability

The patch produced in Example 2 and Lidoderm (manufactured by TEIKOKU SEIYAKU Co. Ltd.) as an existing lidocaine patch were each cut into a circle shape with a diameter of 1.3 cm, and the patches were then attached to a skin portion extracted from the abdominal portion of HWY/Slc male hairless rat (5 weeks old). The skin was set into a vertical diffusion cell, and a test was then initiated using a transdermal absorption test auto-sampler (manufactured by CosMED Pharmaceutical Co. Ltd.). A 0.01 mol/L phosphate buffered saline (pH 7.2 to 7.4) was used as a buffer, and the buffer temperature was set at 32° C. Thereafter, 3, 6, 9, 12, 18, and 24 hours after initiation of the test, an aliquot was extracted from the buffer, and the amount of lidocaine and the amount of prilocaine in the buffer, which had been permeated through the rat skin, were quantified according to HPLC. The sum of the permeated amounts of lidocaine and prilocaine was defined as a drug permeation amount, and the magnification of the present drug permeation amount to the drug permeation amount obtained in the case of using Lidoderm was evaluated. The results obtained by the measurement of cumulative drug skin permeation amounts are shown in FIG. 1, and the results obtained by the measurement of drug skin permeation rates are shown in FIG. 2.

Test Example 2

Evaluation of Analgesic Action in Rat Chung Models

Using Chung models that were neuropathic pain models, analgesic action was evaluated. The rat Chung models were produced in accordance with the method of Kim and Chung (Pain 50(3), 355-363 (1992)). Specifically, using 6-week-old Crl:CD(SD) male rats (8 rats per group), L5 and L6 spinal nerves were exposed under isoflurane-anesthetized conditions, and the central side thereof was strongly ligated with a silk thread (5-0). The wound was sutured, and the rats were then bred for 1 week. Thereafter, the pain threshold of the existing lidocaine patch Lidoderm used as a control formulation and the pain threshold of the patch of Example 2 used as a test substance were measured using Dynamic Plantar Aesthesiometer (manufactured by Ugo Basile). Each patch was attached to the planta of the let limb for 12 hours, and the measurement was carried out immediately after the peeling of the formulation (0 hour) and 2 hours after the peeling. The pain threshold was indicated by a mean value±standard error in each group. The test results are shown in Table 10. It is to be noted that a significant difference was examined using Dunnett's multiple comparison test by the multi-group comparison between the Lidoderm administration group and the Example 2 formulation administration group, and it was determined that there was a significant difference in the case of $P<0.05$ (in Table 10, the symbol * indicates $P<0.05$).

TABLE 10

| | Pain threshold (g) | | |
|---|---|---|---|
| Group | Before administration | Immediately after removal after attachment for 12 hours | Two hours after removal |
| Example 2 | 4.7 ± 0.2 | 9.1 ± 0.2* | 6.8 ± 0.3* |
| Lidoderm | 4.7 ± 0.2 | 6.8 ± 0.2 | 4.8 ± 0.3 |

Analgesic action was evaluated. As a result, it became clear that the pain threshold in the Example 2 patch administration group was a significantly higher value than that in the Lidoderm administration group, both immediately after the peeling of the patch after the attachment thereof for 12 hours, and 2 hours after the peeling, and further that the analgesic action of the patch of Example 2 was sustained for a longer period of time than in the case of Lidoderm. That is to say, it was found that the patch of the present invention has significantly higher therapeutic effects than Lidoderm in the treatment of postherpetic neuralgia, and also that the present patch is useful as a formation for treating superficially localized neuropathic pain.

The invention claimed is:

1. A patch formed from an adhesive layer comprising from 5% by weight to less than 20% by weight of a mixture of lidocaine and another local anesthetic selected from the group consisting of prilocaine, tetracaine, benzocaine, bupivacaine, mepivacaine and combinations thereof, wherein the adhesive layer comprises at least a rubber-based pressure-sensitive adhesive and liquid paraffin and a content of a tackifier in the adhesive layer is 10% by weight or less, and wherein the liquid paraffin is comprised in an amount of from 0.5 times by weight to 2.6 times by weight, based on an amount of the rubber-based pressure-sensitive adhesive, wherein the rubber-based pressure-sensitive adhesive is a mixture of a styrene-isoprene-styrene block copolymer and a styrene-isoprene block copolymer.

2. The patch according to claim 1, wherein the liquid paraffin is comprised in an amount of from 0.7 times by weight to 1.5 times by weight, based on an amount of the rubber-based pressure-sensitive adhesive.

3. The patch according to claim 1, wherein a content of the styrene-isoprene-styrene copolymer in the mixture of a styrene-isoprene-styrene block copolymer and a styrene-isoprene block copolymer is from 15% by weight to 60% by weight.

4. The patch according to claim 1, wherein the liquid paraffin is comprised in an amount of from 2.0 times by weight to 2.6 times by weight, based on an amount of the rubber-based pressure-sensitive adhesive.

5. The patch according to claim 1, wherein a content of the styrene-isoprene-styrene copolymer in the mixture of a styrene-isoprene-styrene block copolymer and a styrene-isoprene block copolymer is 60% by weight or more and 95% by weight or less.

6. The patch according to claim 1, wherein, when a weight of the liquid paraffin to a weight of the rubber-based pressure-sensitive adhesive is defined as y, a weight percent of the styrene-isoprene-styrene copolymer in the mixture of a styrene-isoprene-styrene block copolymer and a styrene-isoprene block copolymer is defined as x, and the base of natural logarithm is defined as e, the patch satisfies the following exponential:

$$0.48e^{0.022\,x} - 0.4 \leq y \leq e^{0.021\,x} + 0.4.$$

7. The patch according to claim 1, wherein said another local anesthetic is prilocaine, tetracaine, benzocaine, or a combination thereof.

8. The patch according to claim 1, wherein a content of the lidocaine in the mixture of lidocaine and another local anesthetic is from 30% by weight to 70% by weight.

9. The patch according to claim 1, wherein a content of the mixture of lidocaine and another local anesthetic is from 5% by weight to less than 15% by weight, based on the total amount of pressure-sensitive adhesive components.

10. The patch according to claim 1, wherein the adhesive layer does not comprise a tackifier.

11. The patch according to claim 1, which is used as a local anesthetic agent.

12. The patch according to claim 1, which is used as an analgesic or a pain therapeutic agent.

13. The patch according to claim 12, which is used as a therapeutic agent for neuropathic pain.

* * * * *